United States Patent
Pandey et al.

(10) Patent No.: US 7,364,873 B2
(45) Date of Patent: Apr. 29, 2008

(54) METHOD FOR MANUFACTURE OF LACTATE BIOSENSING STRIP

(75) Inventors: Manoj Kumar Pandey, New Delhi (IN); Asha Chaubey, New Delhi (IN); Krishan Kant Pande, New Delhi (IN); Rajendra Kumar Sharma, New Delhi (IN); Krishan Kumar Saini, New Delhi (IN); Bansi Dhar Malhotra, New Delhi (IN); Rajesh, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 47 days.

(21) Appl. No.: 11/294,488

(22) Filed: Dec. 6, 2005

(65) Prior Publication Data
US 2007/0087399 A1    Apr. 19, 2007

Related U.S. Application Data

(62) Division of application No. 10/342,303, filed on Jan. 15, 2003.

(51) Int. Cl.
*C12Q 1/26* (2006.01)
(52) U.S. Cl. .................... 435/25; 435/817; 204/403.04
(58) Field of Classification Search .................. 435/25
See application file for complete search history.

(56) References Cited

U.S. PATENT DOCUMENTS 5,707,502 A    1/1998    McCaffrey et al.
5,820,551 A    10/1998    Hill et al.

OTHER PUBLICATIONS

Chaubey et al.,, "Immobilization of Lactate Dehydrogenase on Electrochemically Prepared Polypyrrole-Polyvinylsulphonate Composite Films for Application to Lactate Biosensors", Electrochimica Ata, Elsevier Science Publishers, Barking, GB, vol. 46, No. 5, Jan. 1, 2001, pp. 723-729, XP004225124.

Gerard et al., "Immobilization of Lactate Dehydrogenase on Electrochemically Prepared Polyaniline Films", Electroanalysis, vol. 11, No. 6, May 1999, pp. 450-452, XP009015496.

Gerard et al., "Application of Conducting Polymers to Biosensors"; biosensors & bioelectronics, vol. 17, No. 5, May 2002, pp. 345-359, XP002250769.

Chaubey et al., "Immobilization of Lactate Dehydrogenase on Tetraethylorthosilicate-derived sol-gel films for Application to Lactate Biosensor", Applied Biochemistry and Biotechnology, vol. 96, No. 1-3, Oct. 2001, pp. 292-201, XP009015497, ISSN: 0273-289.

International Search Report dated Aug. 18, 2003.

*Primary Examiner*—Ralph Gitomer
(74) *Attorney, Agent, or Firm*—Nixon & Vanderhye P.C.

(57) ABSTRACT

We provide a lactate biosensing strip comprising a working electrode and a reference electrode, the two electrodes being deposited on an electrically insulated base support, the working electrode being formed by immobilizing lactate oxidase and an electron mediator on an inorganic graphite matrix and the graphite layer being deposited on a silver layer of the working electrode and the reference electrode being formed by depositing silver chloride on a silver layer of the reference electrode.

18 Claims, 4 Drawing Sheets

METHOD FOR MANUFACTURE OF LACTATE BIOSENSING STRIP

RELATED APPLICATION

This is a division of our copending commonly assigned application 10/342,303 filed Jan. 15, 2003 now allowed.

FIELD OF THE INVENTION

The invention relates to a lactate biosensing strip for the measurement of lactate solution. The present invention also relates to a method for the manufacture of a novel lactate biosensing strip and to the use thereof for lactate sensing.

BACKGROUND OF THE INVENTION

Physicians rely on personal examination and clinical laboratory results to determine the presence and concentration of biological analytes in critical care patients. Clinical laboratories offer a wide range of automated systems for high-volume testing and analytical support in a well controlled, high quality environment. However, clinical laboratories can not provide the immediate results needed to properly treat trauma and multi organ dysfunction/failure patients.

To meet the clinical need for immediate test results, several technologies are emerging for testing using reliable, automated analyzers at the patient's bedside including electrochemical biosensors, optical fluorescence sensors, paramagnetic particles for coagulation test systems, and micromachined devices for both chemical and immunochemical testing. These technologies have allowed multi-analyte chemistry panels to be performed rapidly and have addressed previous obstacles such as calibration of test devices.

These tests can be classified as: 1) in vitro, which is performed at the bedside; 2) ex vivo or para vivo, which is performed at wrist-side; and 3) in vivo, which is performed inside the patient. Such tests offer indirect cost efficiencies and savings such as reduced labor costs, decreased blood identification and transport errors, and reduced patient complications.

In vitro or bedside devices are used typically in several departments of the hospital including intensive care units; operating rooms; emergency departments (ER); interventional departments; general patient care departments; and outpatient surgery and ambulatory care units. In vitro diagnostic tests offer a wide range of diagnostic tests, similar to the clinical laboratory. In vitro diagnostic test systems typically are not connected on-line to the patient and require an operator for blood sampling.

Key categories of diagnostic test in the diagnostic market include arterial blood gases, blood chemistries, blood glucose, coagulation, drugs-of-abuse testing, hemoglobin, hematocrit, infectious diseases, and therapeutic drug monitoring. Other categories include cancer markers, cardiac markers, cholesterol detection, immunodiagnostics, infectious disease detection, lactate, and thrombolytic monitoring.

Ex vivo diagnostics use external sensors for on-line real-time testing with little to no blood loss. Typically, sampled blood flows through a closed system to minimize blood contact. Ex vivo systems minimize problems associated with in vivo sensors, including clotting, inaccuracy, calibration drift, and an inability to recalibrate once in the patient. U.S. Pat. No. 5,505,828 discloses an exemplary ex vivo system.

In vivo diagnostics offer considerable potential in the treatment of most critical and unstable patients. Although many companies are developing in vivo sensors, technical hurdles have thus far kept in vivo sensors from common commercial use.

Ex vivo and in vivo diagnostics, since they are on-line systems, can reduce quality control and information integration errors that occur with clinical or in vitro tests. Quality control errors are commonly due to operator errors, not instrument errors or device failures. Exemplary errors include inappropriate specimen volume, inaccurate calibration, use of deteriorated test strips, inadequate validation, insufficient instrument maintenance, bad timing of the test procedure, and use of the wrong materials. Clinical information system integration allows test data collected at the bedside to be put directly into the patient record. This improves the efficiency of the patient management process, allowing the integration of the laboratory's information system and clinical information systems, providing a "seamless" flow of all types of patient information.

Lactate is the byproduct of carbohydrate metabolism and product of glycolysis (pyrovate) is converted into lactate under an aerobic condition i.e. deficiency of oxygen in cells. Lactate estimations are therefore important in respiratory disorder, heart ailment, labor diseases etc. normal concentration of lactate in human blood is in the range of 1.2 to 2.7 mM.

Procedure for lactate determination for example, has employed a variety of chemical and physical technique. Traditional assay involves chemical treatment of lactate in human blood and thereby converting it into color products which can be measured spectrophotometrically, the methods consists in reacting the blood under test with enzyme namely lactate dehydrogenise (LDH). In such process absorbance at 340 nm is measured due to the NADH formation, it becomes a measurement of lactate originally present in blood.

U.S. Pat. No. 6,117,290 discloses an on-line lactate sensor arrangement. The sensor arrangement includes a lactate sensor, a catheter for withdrawing a test sample, and a first fluid flow line provided fluid communication between the lactate sensor and the catheter. The sensor arrangement also includes a source of sensor calibration and anticoagulant solution, and second fluid flow line providing fluid communication between the source of sensor calibration and anticoagulant solution and the lactate sensor.

In practice there are some difficulties in adopting such a detection procedure for use with blood sample. The disadvantage of such methods, include, lack of specificity, difficulty of standardization requirement of large amount of blood and use of unstable and corrosive regents. Such methods also involve optical detection and are therefore expensive and time consuming. Additionally, the samples must be prepared. Another disadvantage is that the measurement of lactate level by prior art methods need to be done in laboratory by qualified personnel.

Asha Chaubey et al disclose in Electrochimica Acta. Vol 46, 723-729 (2000) the immobilization of lactate dehydrogenase on electrochemically prepared polypyrrole polyvinyl sulphonate composite films. The response time reported is about 40 seconds and a shelf life of about 2 weeks under refrigerated conditions. In another disclosure (Asha Chaubey et al Analyticla Chimica Acta Vol 49, 98-103, 2000), the immobilization of lactate dehydrogenase on conducting polyaniline films is disclosed. The linearity of response is shown from 0.1 mM to 1 mM lactate concentration with a shelf life of about 3 weeks under refrigerated conditions. It is preferable to obtain sensors with longer shelf life and shorter response time.

Accordingly, it is important to provide a lactate biosensing strip that can overcome the disadvantages of the prior art without losing out on efficiency and accuracy of measurement.

OBJECTS OF THE INVENTION

The main object of this invention is to provide a novel lactate biosensing strip for the measurement of lactate in aqueous medium.

It is another object of the invention to provide a lactate biosensing strip which performs rapidly and accurately the estimation of lactate in an aqueous medium.

It is yet another object of the invention to provide a lactate biosensing strip which is low cost and is capable of being used by even non-medical persons.

A further object of this invention is an assay, which can be performed without the need for elaborate preliminary treatment of blood sample.

Another object of this invention is to provide a lactate biosensing strip, which has a high activity of 75%.

Still another object of this invention is to provide a lactate-sensing strip, which is capable for providing a reading at site.

SUMMARY OF THE INVENTION

Lactate biosensing strips have many advantages over traditional methods, such as fast response, small size convenience, specificity of response, lack of need of any sample preparation, low cost and high sensitivity of measurement. The main advantage of this sensor over the traditional method is sample operation it can be done by ordinary person.

The present invention provides a lactate biosensing strip for use in the assay of lactate in a sample, said sensor comprising a dry strip sensor of an electrically conducting material having at least:
i. an external surface.
ii. a screen printed reference electrode and
iii. a screen-printed working electrode.

Accordingly, the present invention provides a lactate biosensing strip comprising a working electrode and a reference electrode, the said two electrodes being deposited on an electrically insulated base support wherein the working electrode being formed by immobilizing an enzyme lactate oxidase and an electro mediator on an inorganic graphite matrix and the said graphite layer being deposited on a silver layer and the reference electrode being formed by depositing silver chloride on an another silver layer.

In an another embodiment the biosensing strip further comprises
i. an electrically insulated base support (1),
ii. a pair of first and second silver layers deposited thereon (2) separated by an appropriate space between the two said layers,
iii. a pair of graphite layers, each one of said pair of graphite layers being deposited on one respective silver layer and being electrically connected to said respective silver layer (2),
iv. the first silver layer being covered fully by the respective graphite layer,
v. the second silver layer being covered partly in the middle thereof with the respective graphite layer after leaving the connecting terminal and working zone area uncovered,
vi. the uncovered working zone of said second silver electrode layer being deposited with silver chloride (4),
vii. lactate oxidase being deposited with a mediator on the working zone of graphite layer covering the first silver layer (5),
viii. the said silver/silver chloride layer forming reference electrode (4) and enzyme with mediator layer forming working electrode (5) being supported on said support (1),
ix. the working zone of reference electrode (4) and working electrode (5) being covered with a hydrophilic membrane.

In one embodiment of the invention, the electrically insulated base support used is made of polyvinyl chloride.

In one embodiment of the invention the distance between the silver layers is in the range of 0.5 to 1 mm In another embodiment of the invention, the thickness of each silver layer is in the range of 15 to 25 microns.

In another embodiment of the invention the electron mediator layer comprises a layer of potassium ferricyanide or ferrocene.

In another embodiment of the invention, the hydrophilic membrane is made of nylon or polyester.

In another embodiment of the invention, the working zone are of electrode is a target area used for dispensing the analyte sample In another embodiment of the invention the connecting terminal zone area of electrode is an area used for the connectivity of electrode to an electrometer The lactate biosensing strip of the invention shows an activity of 75% and a response time for lactate detection is in the range of 30 to 40 seconds. The shelf life of the strip of the invention is about 4 months under refrigerated conditions. Under ambient conditions (25 to 30° C.) the shelf life of the biosensing strip is seen to about 2 months. The strip of the invention is disposable.

The invention also relates to a method for the manufacture of a lactate biosensing strip said strip comprising an electrically insulated base support (1), a pair of isolated first and second silver layers deposited thereon (2), a pair of graphite layers, each one of said pair of graphite layers being deposited on one respective silver layer and electrically connected to said respective silver layer (2), the first silver layer being covered fully by the respective graphite layer, the second silver layer being covered partly in the middle thereof with the respective graphite layer leaving the connecting and working zone area of the said layer uncovered, a Ag/AgCl electrode (4) provided on top of the working area of said second silver electrode layer, lactate oxidase deposited with a mediator on the working area of graphite layer covering the first silver layer (5), the said silver/silver chloride electrode (4) and enzyme with mediator working electrode being supported on said support (1), said process comprising (a) depositing a pair of silver layers on an electrically insulated base support by any conventional method;
(b) depositing a pair of graphite layers on said silver layers by any conventional method, each of said silver layers being deposited with one graphite layer, a first graphite layer completely covering the first silver layer, and the second graphite layer covering the second silver layer only in part of the surface thereof that is away from the surface facing the base support;
(c) depositing a silver chloride layer on the second silver layer on the part thereof that is not deposited with a graphite layer to obtain a silver/silver chloride electrode;
(d) adsorbing physically lactate oxidase enzyme with an electron mediator on the first graphite deposited silver layer to obtain a working electrode; and (e) applying an outer hydrophilic membrane on the above said first reference electrode and second working electrode to obtain the desired pair of electrodes on an electrically insulated base support in a single assembly.

In one embodiment of the invention the electrically insulated base support comprises of polyvinyl chloride.

In another embodiment of the invention said silver layer used is applied by the step of screen-printing.

In another embodiment of the invention, said graphite layer used is applied by the step of screen-printing.

In another embodiment of the invention, the sample being tested is an aqueous lactate solution or blood sample in an amount of 25 to 30 µL.

In another embodiment of the invention, the electron mediator used is selected from potassium ferricyanide and ferrocene.

In another embodiment of the invention, connecting terminal zone area of electrode is an area used for the connectivity of electrode to an electrometer In another embodiment of the invention, the hydrophilic membrane is made of nylon or polyester.

BRIEF DESCRIPTION OF THE ACCOMPANYING DRAWINGS

DETAILED DESCRIPTION OF THE INVENTION

Figure 1:
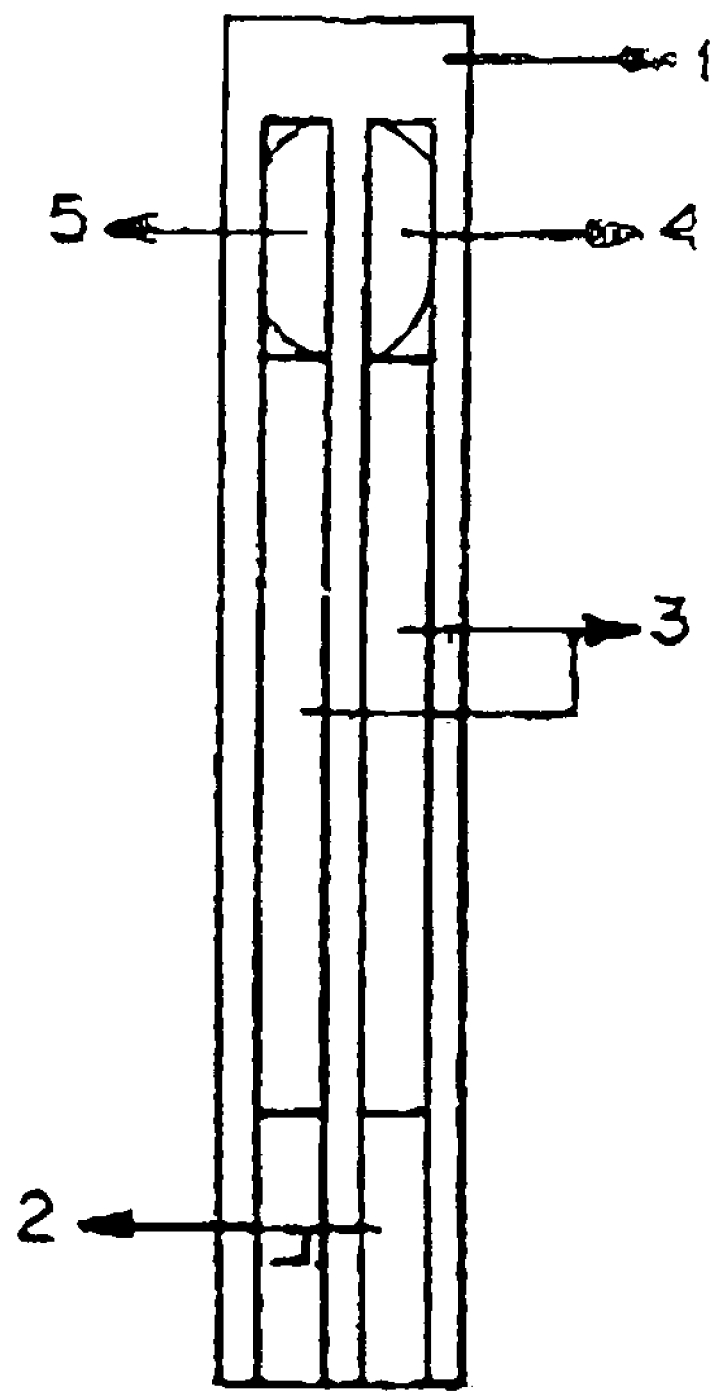
FIG. 1 is a schematic representation of the biosensing strip of the invention.

As shown in FIG. 1, the invention comprises an electrically insulated base support (1) for supporting an electrode assembly (2), (3), (4) and (5). The electrode assembly comprises two electrode systems, a working electrode system (2), (3) and (5) consisting of a silver layer with a graphite layer deposited thereon and an enzyme and mediator layer adsorbed in the inorganic matrix. The other electrode assembly comprises a reference electrode comprising a silver layer partly deposited with a graphite layer and a silver/silver chloride layer thereon FIG. 1 shows the PVC sheet (i) which comprises the supporting substrate for the electrode. Conducting silver tracking (ii) is the screen-printed conducting graphite layer onto the surface of conducting silver tracking (iii) for the connection of the sensor to read out apparatus. The target area consists of the working electrode (iv) and the reference electrode (v) applies to the end of tracking by screen-printing. An insulated layer is applied over the printed electrode to give them protection; the mass can be coated with one or more legends. The conducting graphite track (ii) does not extend to the complete length of the silver track and the reference electrode.

Figure 2:
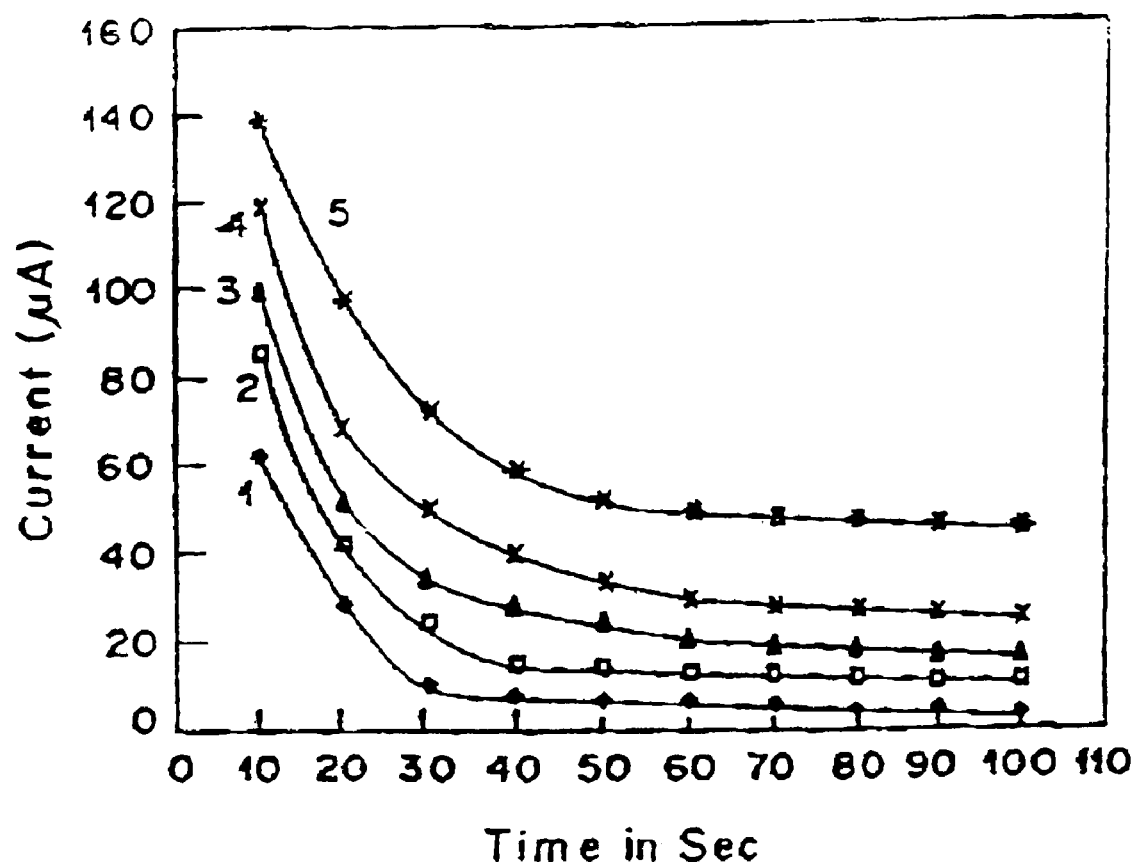
FIG. 2 is the response curve of the lactate biosensing strip of the invention for standard lactate test samples.

To achieve calibration of the biosensing strip, the strip was used to detect currents when the lactate solutions were used in concentrations of 1 to 8 mM. The current measured for each of the concentrations was measured and plotted in FIG. 2. In FIG. 2, curve (1) is the response curve for 1 mM lactate solution, curve (2) is for 2 mM solution, curve (3) is for 4 mM solution, curve (4) is for 6 mM solution and curve (5) is for 8 mM solution. This shows that the biosensing strip of the invention can be used to measure lactate in a blood sample if the range lies in the region of 1 to 8 mM in a subject. The sensitivity of the system in terms of the response time to attain a stable current value was determined by analyzing the strip time variation of current. This comprised initiating current measurement from the time of putting the drop of standard test solution on the strip to the time when the current asymptotically reaches a stable value. It was observed (FIG. 3) that the current attains the stable value in 30 to 40 seconds.

Figure 4:
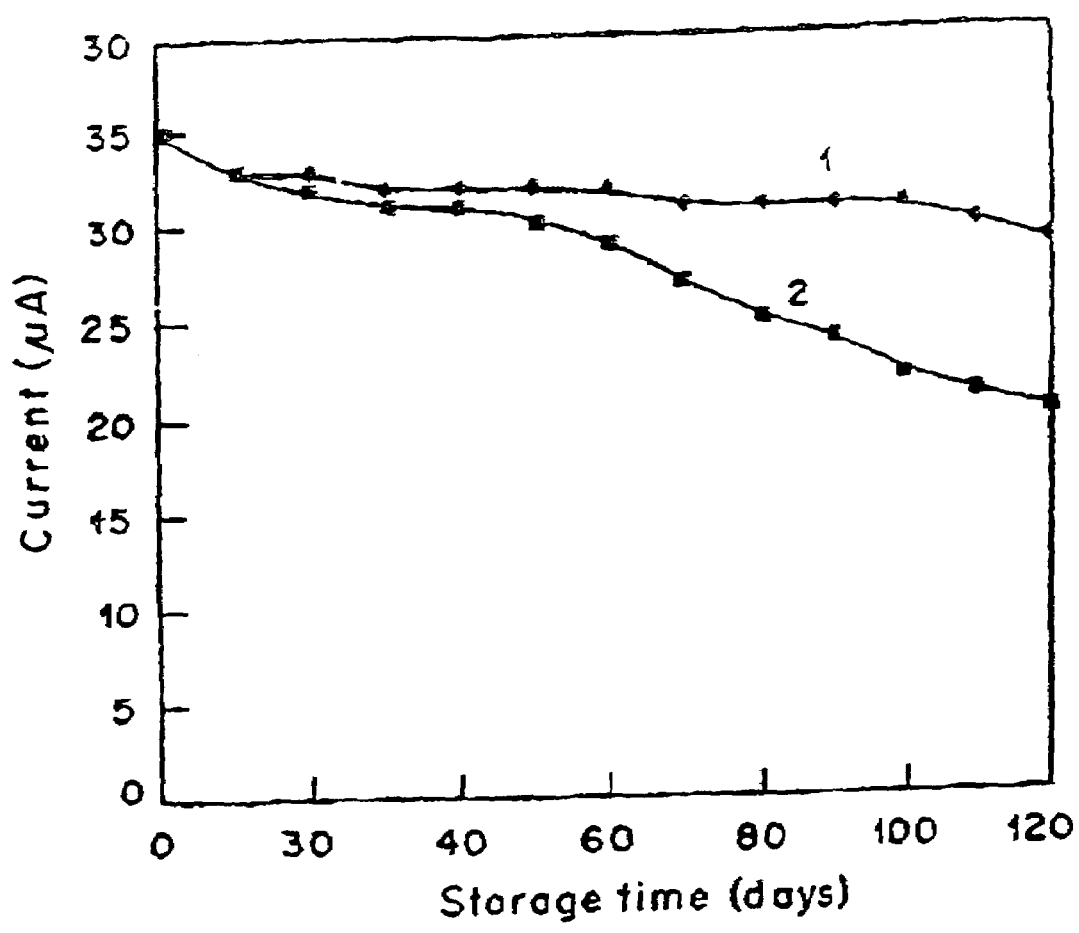
FIG. 4 shows the shelf life stability characteristics of the lactate strip of the invention.

Shelf life characteristics were determined by measuring the current due to a known lactate concentration on strips stored for different periods of time. The data is given in FIG. 4. In FIG. 4, curve (1) is for strips stored under refrigerated conditions (at 4° C.) while curve (2) is for strips stored at 25-30° C.

The invention also provides a process for producing a lactate sensor strip which comprise in forming a first and second electrode on a substrate by applying a layer of silver for each of said electrodes in said electrode, applying a layer graphite on the handling zone of said second electrode to silver chloride, applying a mediator and enzyme on the graphite layer of the working zone of the first electrode. An outer hydrophilic membrane is applied zone of said first electrode. The silver layers and the graphite layers are preferably applied by the step of screen-printing.

The main feature of this invention is that the sensor is a dry strip sensor. It is found that a similar mix of reagents employed in a wet sensor system did not give good result across a desired range of detectable lactate concentration.

This invention comprises a substrate for supporting an electrode assembly said electrode assembly comprising two electrode systems, one working electrode and another one as a reference electrode supported on said substrate and disposed in a spaced relationship to each other. The lactate sensing strip comprising of a substrate for supporting a first or working electrode and second or reference electrode, said electrode disposed in a spaced relationship to each other.

The first electrode is a working electrode and has a terminal extending in to a working zone through a handling zone. The second electrode is a reference electrode and has a terminal extending in to a working zone through a handling zone. In both cases, the respective terminals are of a material different to the base conducting layer of said first and second electrodes.

Commercially obtained lactate oxidase is mixed in a phosphate buffer, then proper amount of this solution is injected onto a preprinted working electrode. This solution is allowed to dry in allow temperature, followed by
i. printing of conducting tracking
ii. printing of reference electrode
iii. printing of working electrode
iv. fixing of membrane onto electrode.

The working and reference electrode each comprise a base conducting layer of silver material along the handling and working zone. A graphite layer is deposited on the silver layer of the working electrode and extends to the terminal; the graphite layer is applied on the handling zone of the reference electrode and extends to the terminal. Ag/AgCl is deposited on the target area of the reference electrode. Working electrode comprising conducting surface carrying mediator compound and lactate oxidase enzyme. Mediator compound transfer electrodes from the enzyme to the electrode, when such catalytic activity takes place. A hydrophilic membrane must be provided on the working zone of said electrode. It appears that the surfactant serves to break up the lipoprotein complex of blood and lactate is then oxidized to the pyruvate by the lactate oxidase. The mediator compound is electrochemically reduced at the electrode producing a current measurable at the electrode, which current is relative to the activity of the lactate oxidize and hence the amount of lactate present in the sample this current is generated through a serious of coupled reactions $$\text{L-Lactate} + \text{LOD}_{(ox)} \text{ - - - } \text{Pyruvate} + \text{LOD}_{(red)}$$

$$\text{LOD}_{(red)} + \text{Me}_{(ox)} \text{ - - - } \text{LOD}_{(ox)} + \text{Me}_{(re)}$$

The redox mediator is oxidized at the base electrode and the current proportional to the lactate concentration. The current can be measured by any conventional electronic system.

The following examples are given by the way of illustration and therefore should not constitute to limit the scope of the present invention.

EXAMPLE 1

Preparation of Graphite Paste with Mediator 100 mg of graphite powder and polyvinyl pyrrolidon (binder) was mixed with 0.01M Potassium ferricyanide (mediator) in ethylene glycol monobutyl ether to prepare screen printable working electrode graphite paste.

EXAMPLE 2

Preparation of Dry Strip

Commercially obtained lactate oxidase solution (2 μL) containing 2 U of lactate oxidase was physically adsorbed on the mediator mixed graphite electrode strip and was kept over night to dry at 25° C. The dry strip electrode was covered with a hydrophilic nylon membrane. Before the membrane was applied, it was placed in 10% surfactant (Tween 80) solution in distilled water for some time the dried membrane was then fixed over the strip.

EXAMPLE 3

Preparation of Lactate Standard Lactate Solutions

Stock lactate solution 10 mM was prepared in 0.1M phosphate buffer. Standard solutions of 2 mM, 4 mM, 6 mM and 8 mM were prepared by diluting the stock solution with phosphate buffer.

EXAMPLE 4

Preparation of Enzyme Stock Solution 15 mg of enzyme lactate oxidase was dissolved in 100 μl of 0.1M phosphate buffer to get the concentration 5 U/μl to get the working enzyme solution, the stock solution was further diluted to 1 U/μl.

EXAMPLE 5

Immobilization of Enzyme on the Mediator Mixed Graphite Dry Strip

2 μl of enzyme solution containing 2 U of lactate oxidase was physically adsorbed on the mediator mixed graphite electrode strip and was kept over night to dry at 25° C. The said dry strip electrode was covered by a hydrophilic nylon membrane. Before applying the membrane, it was placed in 10% surfactant (Tween 80) solution in distilled water for some time and then dried membrane was fixed over the strip.

EXAMPLE 6

Enzyme Activity

Sigma protocol for activity of lactate oxidase was used to estimate the lactate oxidase activity. The basic principle is that lactate oxidase converts l-lactate to pyruvate and $H_2O_2$. $H_2O_2$ is subsequently converted into a colored dye by peroxidase in the presence of 4-amino antipyrine (4AAP) and dimethylaniline(DMA).

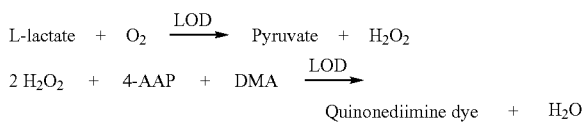

In the optimum conditions of temperature=37° C. and pH=6.5, the dye absorbs at 565 nm at the light path of 1 cm.

The activity of the immobilized enzyme was calculated according to the following formula:

$$U \text{ cm}^{-2} = AV/\epsilon t\, s$$

Where A is the change in absorbance before and after incubation

V is the total volume (3 ml)

$\epsilon$ is the milimolar extinction coefficient of Quinonediimine dye at 565 nm (35.33)

t is the reaction time (10 min)

s is the surface area of the enzyme electrode

The enzyme activity of immobilized LOD on the working graphite strip was found to be 75%.

EXAMPLE 7

Amperometric Response Studies

Figure 3:
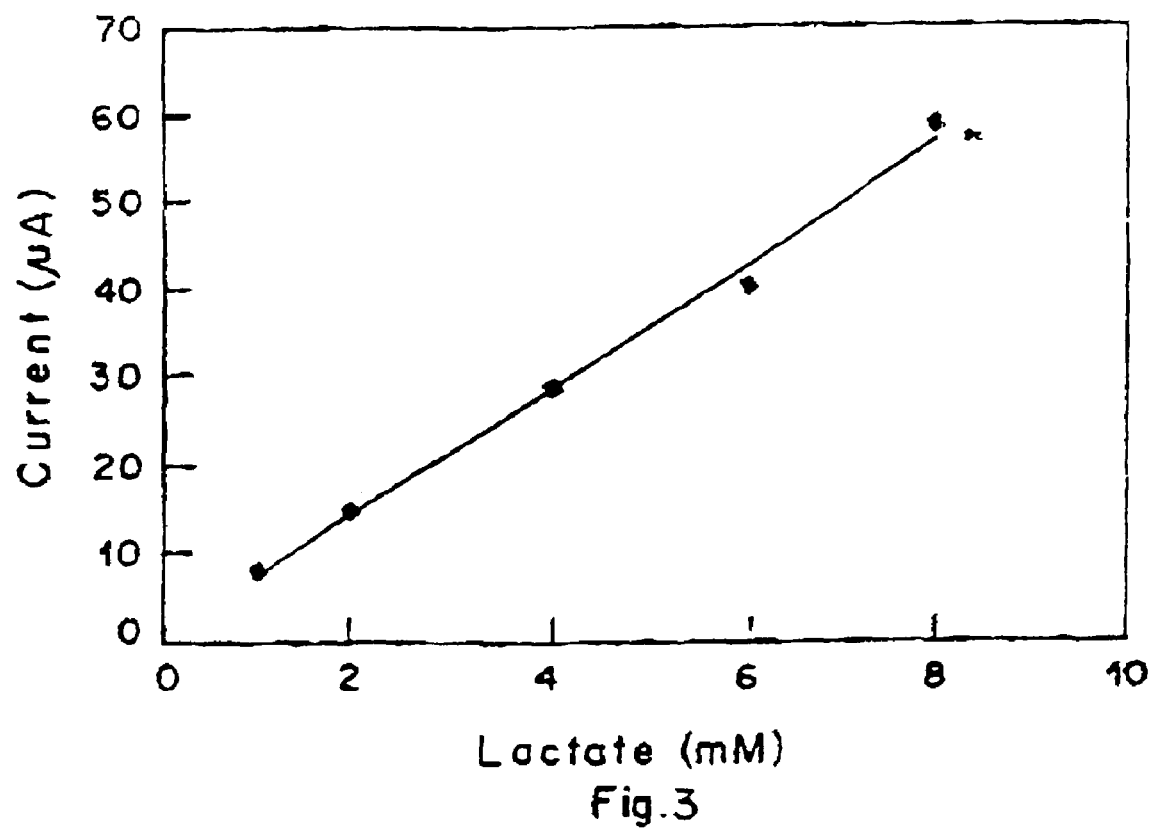
FIG. 3 shows the calibration curve for the sensor against standard lactate test samples prepared in a laboratory.

The lactate biosensing strip comprising enzyme(LOD) immobilized on graphite as working electrode and Ag/AgCl reference electrode is connected to the input of the electrometer was polarized at a bias voltage of 0.4V for the measurement of amperometric calibration response to lactate (1-8 mM)(FIG. 2). A maximum current of 60 μA was obtained for 8 mM lactate solution above which no significant change in current could be observed. The response time for lactate solution (1-8 mM) was found to be 40 seconds for each concentration of lactate (FIG. 3). Results were found to be reproducible to within 5%. Following principle was involved in the amperometric measurements.

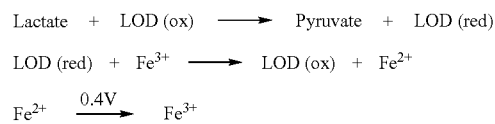

ADVANTAGES OF THE INVENTION

1. The lactate biosensing strip provides a quick estimation of lactate in a sample 2. the shelf life of the sample is 4 months under refrigerated conditions.

3. the strip has a linear response in a lactate concentration of 1 to 8 mM.

4. the strip is disposable without causing any environmental hazard.

5. the strip is easily used even by people without any formal medical training.

We claim:

1. A method for preparing a lactate biosensing strip comprising an electrically insulated base support (1), a pair of isolated first and second silver layers deposited thereon (2), a pair of graphite layers, each one of said pair of graphite layers being deposited on one respective silver layer and electrically connected to said respective silver layer (2), the first silver layer being covered fully by the respective graphite layer, the second silver layer being covered partly in the middle thereof with the respective graphite layer after leaving the terminal and working zone uncovered, a Ag/AgCl electrode (4) provided on top of the working zone of said second silver electrode layer, lactate oxidase deposited with an electron mediator on the working zone of graphite layer covering the first silver layer (5), the silver/silver chloride electrode (4) and enzyme with mediator layer working electrode (5) being supported on said support (1), the working zone of silver/silver chloride reference electrode (4) and working electrode (5) being covered with a hydrophilic membrane, said lactate biosensing strip being disposable, said method comprising:
(a) depositing a pair of silver layers on an electrically insulated base support;
(b) depositing two graphite layers on each of said two silver layers, each of said two silver layers being deposited with one graphite layer, a first graphite layer completely covering the first silver layer, and the second graphite layer covering the second silver layer only in part of the surface thereof that is away from the surface facing the base support;
(c) depositing a silver chloride layer on the second silver layer on the part thereof that is not deposited with a graphite layer to obtain a silver/silver chloride electrode;
(d) adsorbing physically lactate oxidase enzyme with an electron mediator on the first graphite deposited silver layer to obtain a working electrode; and
(e) applying an outer hydrophilic membrane on said first reference electrode and second working electrode to obtain a pair of electrodes on an electrically insulated base support in a single assembly.

2. The method as claimed in claim 1, wherein the electrically insulated base support is polyvinyl chloride.

3. The method as claimed in claim 1, wherein the silver layer is applied by screen-printing.

4. The method as claimed in claim 1, wherein the graphite layer is applied by screen-printing.

5. The method as claimed in claim 1, further comprising testing a sample which is an aqueous lactate solution or blood sample in an amount of 25 to 30 µL.

6. The method as claimed in claim 1, wherein the electron mediator is potassium ferricyanide or ferrocene.

7. The method as claimed in claim 1, wherein a working zone of an electrode is a target area used for dispensing an analyte sample.

8. The method as claimed in claim 1, wherein a connecting terminal of the reference electrode is an area used for connecting the reference electrode to an electrometer.

9. The method as claimed in claim 1, wherein the hydrophilic membrane is made of nylon or polyester.

10. A method for preparing a two electrode biosensing strip for measuring lactate, said method comprising:
(a) depositing a pair of silver layers on an electrically insulated base support;
(b) depositing a pair of graphite layers on said silver layers, each of said silver layers being deposited with one graphite layer, a first graphite layer completely covering the first silver layer, and a second graphite layer covering only a part of the second silver layer that is away from the surface facing the base support;
(c) depositing a silver chloride layer on a part of the second silver layer that is not deposited with a graphite layer to obtain a reference electrode;
(d) adsorbing physically lactate oxidase with an electron mediator on the first graphite layer to obtain a working electrode; and
(e) covering said reference electrode and said working electrode with a hydrophilic membrane to obtain said two-electrode biosensing strip in a single assembly.

11. The method as claimed in claim 10, wherein the electrically insulated base support is polyvinyl chloride.

12. The method as claimed in claim 10, wherein each silver layer is applied by screen-printing.

13. The method as claimed in claim 10, wherein each graphite layer is applied by screen-printing.

14. The method as claimed in claim 10, further comprising testing a sample which is an aqueous lactate solution or blood sample in an amount of 25 to 30 µL.

15. The method as claimed in claim 10, wherein the electron mediator is potassium ferricyanide or ferrocene.

16. The method as claimed in claim 10, wherein a working zone of an electrode is a target area used for dispensing an analyte sample.

17. The method as claimed in claim 10, wherein a connecting terminal of the reference electrode is an area used for connecting the reference electrode to an electrometer.

18. The method as claimed in claim 10, wherein the hydrophilic membrane is made of nylon or polyester.

* * * * *